United States Patent
Hamada et al.

(10) Patent No.: US 7,217,835 B2
(45) Date of Patent: May 15, 2007

(54) PRODUCTION METHOD OF O-SUBSTITUTED TYROSINE COMPOUND

(75) Inventors: Takayuki Hamada, Kawasaki (JP); Masanobu Yatagai, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 84 days.

(21) Appl. No.: 10/937,345

(22) Filed: Sep. 10, 2004

(65) Prior Publication Data

US 2005/0283021 A1   Dec. 22, 2005

(30) Foreign Application Priority Data

Jun. 17, 2004  (JP) .............................. 2004-180265

(51) Int. Cl.
  *C07C 229/00*  (2006.01)
(52) U.S. Cl. ..................................... 562/444
(58) Field of Classification Search ................. 562/444
  See application file for complete search history.

(56) References Cited

U.S. PATENT DOCUMENTS 6,093,696 A * 7/2000 Head et al. .................... 514/19
6,559,335 B2 * 5/2003 Kumar et al. ................. 560/61

FOREIGN PATENT DOCUMENTS

WO    WO 02/24625       3/2002
WO    WO0224625 A2 *    3/2002
WO    WO 0224625 A2 *   3/2002

OTHER PUBLICATIONS

Green T W "Protective groups in Organic Synthesis" John Wiley and Sons 1991 (please see pp. 445-448).*
Lipshutz Et al Organic Syntheses Coll. vol. 8,p. 33 (1993).*
Ian Lewis, et al., "A Novel Somatostatin Mimic with Broad Somatotropin Release Inhibitory Factor Receptor Binding and Superior Therapeutic Potential", Journal of Medicinal Chemistry, vol. 46, No. 12, 2003, pp. 2334-2344.
Christian Wolf, et al., "Enantioselective alkylation of aldehydes promoted by (S)-tyrosine-derived β-amino alcohols", Tetrahedron: Asymmetry, vol. 13, No. 16, 2002, pp. 1733-1741.
Shiroh Futaki, et al., "Sulphur Trioxide/Thiol: A Novel System for the Reduction of Methionine Supphoxide", Journal of Chemical Society Parkin Transaction, vol. 3, 1990, pp. 653-658.

* cited by examiner

*Primary Examiner*—Thurman K. Page
*Assistant Examiner*—Lalitha Nagubandi
(74) *Attorney, Agent, or Firm*—Oblon, Spivak, McClelland, Maier & Neustadt, P.C.

(57) ABSTRACT

The present invention relates to a method of producing a compound represented by the formula [I] or a salt thereof, which comprises reacting a compound represented by the formula [II] or a salt thereof with a compound represented by the formula [III] or a salt thereof, in the presence of a base, in alcohol, and provides a production method of an O-substituted tyrosine compound, which is superior in productivity, versatility and safety, and economically and industrially useful:

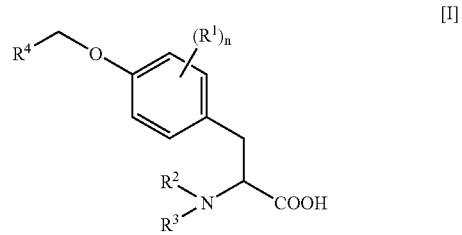

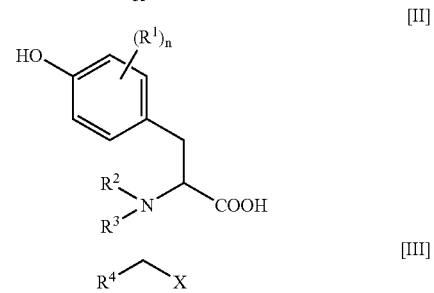

wherein each symbol is as defined in the specification.

27 Claims, No Drawings

PRODUCTION METHOD OF O-SUBSTITUTED TYROSINE COMPOUND

FIELD OF THE INVENTION

The present invention relates to a production method of an O-arylmethylene- or O-(hetero ring-methylene)-substituted tyrosine compound.

BACKGROUND OF THE INVENTION

An O-arylmethylene- or O-(hetero ring-methylene)-substituted tyrosine compound (sometimes to be abbreviated simply as an O-substituted tyrosine compound in the present specification) is useful as an intermediate for the production of, for example, a somatostatin secretion inhibitor as a pharmaceutical agent, and the like (e.g., Journal of Medicinal Chemistry, US, vol. 46, pp. 2334–2344 (2003)).

As a production method of an O-substituted tyrosine compound, for example, methods (1)–(3) shown below, and the like can be mentioned.

(1) WO 02/24625 discloses a method comprising reacting tyrosine with benzyl chloride, in the presence of $CuSO_4$, under basic conditions:

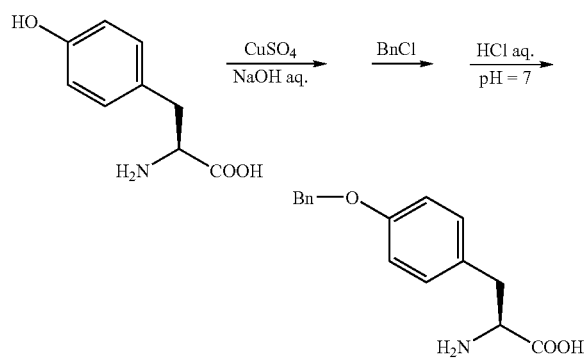

wherein Bn is a benzyl group.

The above-mentioned method achieves a reaction yield of less than 70% and cannot produce O-substituted tyrosine in a high yield. It has been found that, when a halide of a nitrogen-containing compound (e.g., 2-picolyl chloride (i.e., pyridin-2-ylmethylene chloride) and the like) is used instead of benzyl chloride, the reaction proceeds but, since copper is chelated to nitrogen atom in the resulting product and the chelation cannot be solved at a neutral point (pH=7), the reaction yield further decreases. Therefore, the above-mentioned method is unsuitable for production of an O-substituted tyrosine compound with a substituent containing hetero atom, such as nitrogen atom and the like, and poor in versatility.

(2) Tetrahedron Asymmetry, UK, vol. 13, No. 16, pp. 1733–1741 (2002) discloses a method comprising reacting tyrosine, wherein both amino group and carboxyl group are protected, with benzyl bromide, in the presence of $K_2CO_3$ or $Cs_2CO_3$, using acetone as a solvent:

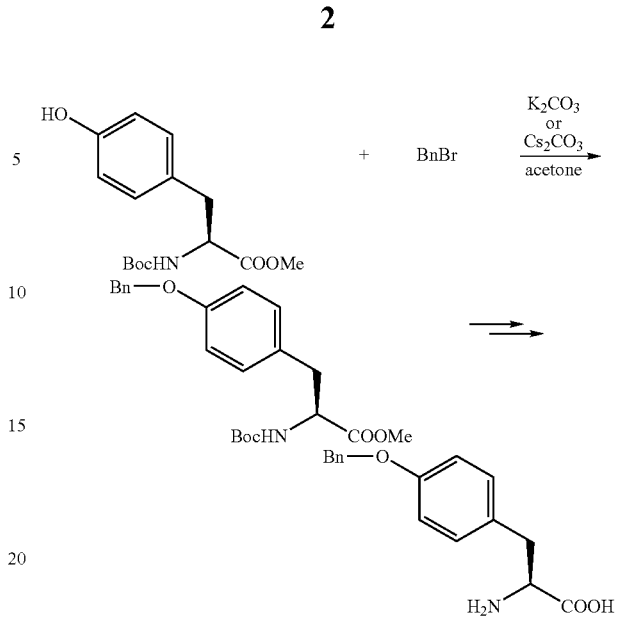

wherein Boc is a tert-butoxycarbonyl group, Me is a methyl group and Bn is a benzyl group.

The above-mentioned method is generally used as a production method of an O-substituted tyrosine compound in a high yield and widely applicable to other substituents.

However, since the above-mentioned method requires, for example, purification by column chromatography to remove BnBr used in excess and by-products, and further requires protection and deprotection steps of the amino group and the carboxyl group of tyrosine, which increases the number of steps and is complicated. In fact, the carboxyl group is methyl-esterified, then the amino group is protected with Boc, the hydroxyl group is subjected to the benzylation, then the protected carboxyl group is deesterified, and the protected amino group is deprotected to give O-benzyl substituted tyrosine. Therefore, this method is not superior in productivity.

(3) Journal of Chemical Society Parkin Transaction 1, UK, vol. 3, pp. 653–658 (1990) discloses a method comprising reacting an amino-protected tyrosine with bromobenzyl compound (Bn-Br), in the presence of sodium hydride (NaH), using N,N-dimethylformamide (DMF) as a solvent:

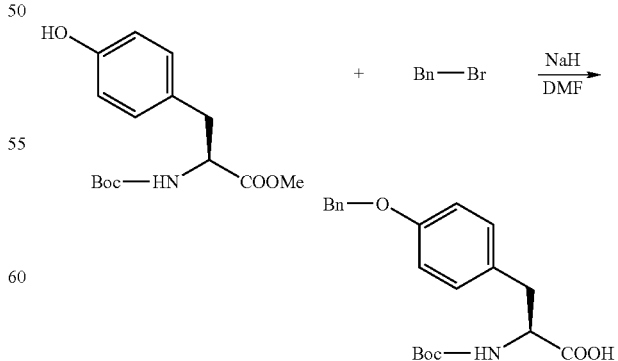

wherein Boc is a tert-butoxycarbonyl group and Bn-Br is 4-(methylthio)benzyl bromide.

DMF to be used as a solvent in the above-mentioned method is expensive, dangerous, highly toxic and is not generally suitable for the industrial production of an O-substituted tyrosine compound.

In addition, DMF has a high boiling point (153° C.) and removal of DMF solvent after the completion of the reaction is not industrially easy. Without removal of the solvent, the yield of crystal precipitation to give an object product decreases.

Moreover, a bromo compound (Bn-Br) to be used for the above-mentioned method is expensive and economically unpreferable. When an economical chloro compound (Bn-Cl) is used as an alternative, the reactivity thereof is lower than the bromo compound, and the reaction does not proceed enough. Thus, these methods have been found to be poor in versatility.

In the above-mentioned method, NaH difficult to handle even in an oil dispersion is used in a powder state, and therefore, the above-mentioned method is highly dangerous and is not suitable for the industrial production.

In the above-mentioned conventional art, method (1) poses problems in the yield, productivity and versatility, method (2) requires many steps and difficult purification and has a problem in productivity. The method (3) uses NaH problematic in safety, and expensive DMF as a solvent, posing a problem in economic aspect. Furthermore, method (3) poses problems of difficult removal of DMF after the completion of the reaction, and the like.

Accordingly, there is a high demand in this field for a production method of an O-substituted tyrosine compound, which is superior in productivity, versatility and safety, and useful economically and industrially.

SUMMARY OF THE INVENTION

An object of the present invention is to provide a production method of an O-substituted tyrosine compound, which is superior in productivity, versatility and safety, and useful economically and industrially.

In view of the above-mentioned problems, the present inventors have conducted intensive studies and found that, by O-substitution reaction of a tyrosine compound in an economical alcohol, in the presence of a base, O-substituted tyrosine compound can be obtained in a high yield, which resulted in the completion of the present invention.

Accordingly, the present invention provides the following.

(1). A method of producing a compound represented by the formula [I] or a salt thereof:

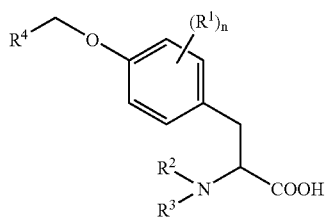

wherein
$R^1$ is each independently a halogen atom, an alkyl group, an alkoxy group or a hydroxy group,
$R^2$ and $R^3$ are each independently a hydrogen atom or an amino-protecting group,
$R^4$ is an optionally substituted aryl group or an optionally substituted hetero ring group, and
n is an integer of 0–4,
provided that $R^2$ and $R^3$ are not simultaneously hydrogen atoms,
wherein said method comprises reacting a compound represented by the formula [II] or a salt thereof:

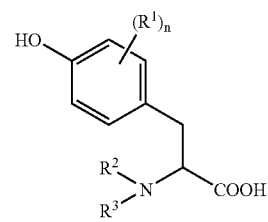

wherein
$R^1$, $R^2$, $R^3$ and n are as defined above,
with a compound represented by the formula [III] or a salt thereof:

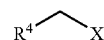

wherein
$R^4$ is as defined above, and
X is a halogen atom, a toluenesulfonyloxy group, a methanesulfonyloxy group or a trifluoromethanesulfonyloxy group,
in the presence of a base, in alcohol.

(2). The production method of (1), wherein the alcohol is selected from the group consisting of methanol, ethanol, isopropanol and tert-butanol.

(3). The production method of (2), wherein the alcohol is methanol.

(4). The production method of (1), wherein the base is alkali metal alkoxide.

(5). The production method of (4), wherein the alkali metal alkoxide is selected from the group consisting of sodium methoxide, sodium ethoxide, sodium isopropoxide and sodium tert-butoxide.

(6). The production method of (5), wherein the alkali metal alkoxide is sodium methoxide.

(7). The production method of (1), wherein the reaction is carried out, in the presence of sodium methoxide, in methanol.

(8). The production method of (1), wherein n is 0.

(9). The production method of (1), wherein the amino-protecting group for $R^2$ or $R^3$ is deprotected with an acid.

(10). The production method of (1), wherein the amino-protecting group for $R^2$ or $R^3$ is selected from the group consisting of a tert-butoxycarbonyl group, a benzyloxycarbonyl group, a methoxycarbonyl group, an acetyl group, a benzoyl group and a benzyl group.

(11). The production method of (1), wherein X is a halogen atom.

(12). The production method of (11), wherein the halogen atom is a chlorine atom or a bromine atom.

(13). The production method of (1), wherein said reacting is at a temperature ranging from 20 to 50° C.

(14). The production method of (1), further comprising washing said compound of formula [I] or salt thereof to remove said compound of formula [III] or salt thereof.

(15). The production method of (14), wherein said washing comprises addition of water and one or more suitable solvent.

(16). The production method of (15), wherein said solvent is selected from the group consisting of heptane, toluene, and dichloromethane.

(17). The production method of (1), further comprising purifying said compound represented by the formula [I], or a salt thereof.

(18). The production method of (1), wherein, when present, said alkyl is a straight, branched or cyclic alkyl group having 1 to 6 carbon atoms.

(19). The production method of (1), wherein, when present, said alkoxy is a straight, branched or cyclic alkoxy group having 1 to 6 carbon atoms.

(20). The production method of (1), wherein the α-carbon of the compound of at least one of [II] or [III], or a salt thereof, is in an L-form.

(21). The production method of (1), wherein the compound of formula [I] or salt thereof is N-Boc-tyrosine or N-Ac-tyrosine.

(22). The production method of (1), wherein said compound of formula [III] or salt thereof is added at a concentration ranging from 1 to 2 mol per 1 mol of the compound of formula [II] or salt thereof.

(23). The production method of (1), wherein said alcohol is present in an amount ranging from 1 to 10 L per 1 kg of compound of formula [II] or salt thereof.

(24). The production method of (1), wherein said base is present in an amount ranging from 2 to 5 mol per 1 mol of formula [II] or salt thereof.

(25). The production method of (1), further comprising a reaction promoter in a concentration ranging from 0.01 to 0.5 g per 1 g of compound of formula [II] or salt thereof.

(26). The production method of (25), wherein said reaction promoter is selected from the group consisting of n-Bu$_4$NI, KI, and NaI.

(27). The production method of (1), wherein said reacting is for a time ranging from 1 hour to 120 hours.

DETAILED DESCRIPTION OF THE INVENTION

The present invention provides the following effects as compared to the conventional art.
1. Since the reaction is carried out in alcohol in this production method, the reaction temperature can be set low (ca. 20° C.–50° C.), the method can be also applied to a compound unstable at a high temperature as compared to that of the conventional art using DMSO (reaction temperature about 650° C., boiling point 189° C.) and the like. In addition, since the reaction can be carried out at a lower temperature than conventional temperatures, the production cost can be reduced.
2. Since the reaction is carried out in alcohol in this production method, DMF used in conventional art, which is expensive, having a high boiling point, dangerous and highly toxic, does not need to be used.
3. The present production method does not require use of dangerous NaH.
4. One pot reaction (i.e., small number of steps).
5. After the completion of the reaction, by adding water and washing with a suitable solvent (e.g., heptane, toluene, dichloromethane etc.), compound [III] used in excess and by-products can be removed easily. In addition, since the object product is crystallized by neutralization, a highly pure object compound can be obtained by merely filtering the crude crystals, and a complicated purification step such as column chromatography and the like is not necessary.
6. The reaction can be carried out in a high yield without protecting the carboxyl group of tyrosine.

According to the present invention, a production method of an O-substituted tyrosine compound, which is superior in productivity, versatility and safety, and economically and industrially useful, can be provided.

BEST MODE FOR EMBODYING THE INVENTION

The terms used in the present specification are defined in the following.

The "halogen atom" means a fluorine atom, a chlorine atom, a bromine atom or an iodine atom.

The "alkyl group" means a straight, branched or cyclic alkyl group having 1 to 6 carbon atoms, such as methyl group, ethyl group, propyl group, isopropyl group, cyclopropyl group, butyl group, isobutyl group, sec-butyl group, tert-butyl group, cyclobutyl group, pentyl group, tert-pentyl group, cyclopentyl group, hexyl group, cyclohexyl group and the like.

The "alkoxy group" means a straight, branched or cyclic alkoxy group having 1 to 6 carbon atoms, such as methoxy group, ethoxy group, propoxy group, isopropoxy group, cyclopropoxy group, butoxy group, isobutoxy group, sec-butoxy group, tert-butoxy group, cyclobutoxy group, pentyloxy group, tert-pentyloxy group, cyclopentyloxy group, hexyloxy group, cyclohexyloxy group and the like.

The "amino-protecting group" is not particularly limited as long as it is an amino-protecting group generally used, such as those described in Protective Groups in Organic Synthesis, published by John Wiley and Sons (1980) and the like.

The "amino-protecting group" is one that is preferably deprotected with an acid, more preferably tert-butoxycarbonyl group, benzyloxycarbonyl group, methoxycarbonyl group, acetyl group, benzoyl group or benzyl group, particularly preferably tert-butoxycarbonyl group or acetyl group.

The "aryl group" of the "optionally substituted aryl group" means an aryl group having 6 to 10 carbon atoms, such as phenyl group, naphthyl group and the like.

The "aryl group" optionally has 1 to 5 substituents at substitutable positions thereof.

As the "substituent", a halogen atom (e.g., fluorine atom, chlorine atom, bromine atom, iodine atom and the like), an alkyl group (same as the above-mentioned "alkyl group", such as methyl group, ethyl group, isopropyl group, tert-butyl group and the like), an alkoxy group (same as the above-mentioned "alkoxy group", such as methoxy group, ethoxy group, isopropoxy group, tert-butoxy group and the like), a nitro group, a dimethylamino group, an aryl group (same as the above-mentioned "aryl group", such as phenyl group and the like) and the like can be mentioned.

The "hetero ring group" of the "optionally substituted hetero ring group" means a 5- to 10-membered saturated or unsaturated hetero ring group containing, besides carbon atoms, 1 to 3 hetero atoms selected from the group consisting of nitrogen atom, oxygen atom and sulfur atom, and, for example, pyrrolidinyl group, tetrahydrofuranyl group, tetrahydrothiofuranyl group, piperidinyl group, tetrahydropyranyl group, tetrahydrothiopyranyl group, piperazinyl group, morpholinyl group, thiomorpholinyl group, pyridinyl group, pyrazinyl group, pyridazinyl group, pyrrolyl group, furyl group, thienyl group, imidazolyl group, oxazolyl group, thiazolyl group and the like can be mentioned.

The "hetero ring group" optionally has 1 to 4 substituents at substitutable positions thereof.

As the "substituent", an alkyl group (same as the above-mentioned "alkyl group", such as methyl group, ethyl group, propyl group, isopropyl group, butyl group, sec-butyl group, tert-butyl group, cyclohexyl group and the like), an alkenyl group (e.g., alkenyl group having 2 to 6 carbon atoms such as allyl group and the like), an aryl group (same as the above-mentioned "aryl group", such as phenyl group and the like) and the like can be mentioned.

The "optionally substituted hetero ring group" is preferably pyridinyl group, and particularly preferably pyridin-2-yl group.

In the compound represented by the above formula [I] or [II], the position of $R^1$ is not particularly limited.

n is an integer of 0–4, preferably 0, 1 or 2, more preferably 0 or 1, and particularly preferably 0.

$R^1$ is independently a halogen atom, an alkyl group, an alkoxy group or a hydroxy group, preferably a halogen atom or a hydroxy group.

As a halogen atom for $R^1$, a bromine atom is particularly preferable.

$R^2$ and $R^3$ are each independently a hydrogen atom or an amino-protecting group. In the present invention, $R^2$ and $R^3$ are not simultaneously hydrogen atoms.

The amino-protecting group for $R^2$ or $R^3$ is not particularly limited, but it is preferably an amino-protecting group to be deprotected with an acid, more preferably selected from the group consisting of tert-butoxycarbonyl group, benzyloxycarbonyl group, methoxycarbonyl group, acetyl group, benzoyl group and benzyl group. It is particularly preferably tert-butoxycarbonyl group or acetyl group.

$R^4$ is an optionally substituted aryl group or an optionally substituted hetero ring group, preferably optionally substituted phenyl group or optionally substituted pyridinyl group (e.g., pyridin-2-yl group and the like), more preferably phenyl group or pyridinyl group, and particularly preferably phenyl group or pyridin-2-yl group.

X is a halogen atom, a toluenesulfonyloxy group, a methanesulfonyloxy group or a trifluoromethanesulfonyloxy group, preferably a halogen atom, more preferably a chlorine atom or a bromine atom.

The present invention is explained in more detail by referring to the following scheme:

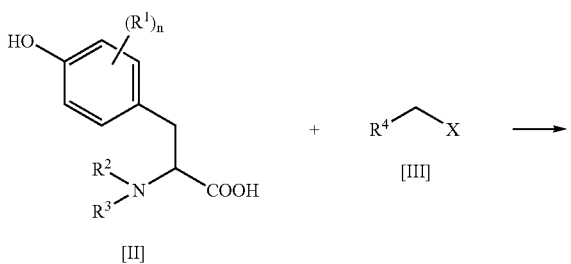

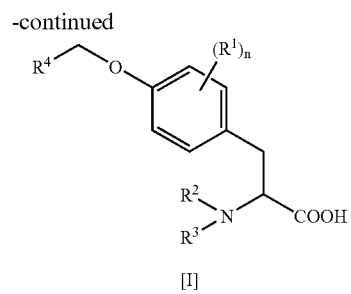

In the scheme, each symbol is as defined above.

The present invention relates to a method of producing a compound represented by the formula [I] (hereinafter sometimes to be abbreviated as compound [I]) or a salt thereof, which comprises reacting a compound represented by the formula [II] (hereinafter sometimes to be abbreviated as compound [II]) or a salt thereof with a compound represented by the formula [III] (hereinafter sometimes to be abbreviated as compound [III]) or a salt thereof, in the presence of a base, in alcohol.

As the salts of compound [I] or [II], for example, salts with inorganic bases, such as alkali metal salts (e.g., sodium salt, potassium salt and the like), alkaline earth metal salts (e.g., calcium salt, magnesium salt and the like), ammonium salt and the like; salts with organic bases such as organic amine salts (e.g., triethylamine salt, pyridinate, picolinate, ethanolamine salt, triethanolamine salt, dicyclohexylamine salt, N,N'-dibenzylethylenediamine salt and the like) and the like; inorganic acid addition salts (e.g., hydrochloride, hydrobromide, sulfate, phosphate and the like); organic carboxylic or sulfonic acid addition salts (e.g., formate, acetate, trifluoroacetate, maleate, tartrate, citrate, fumarate, methanesulfonate, benzenesulfonate, toluenesulfonate and the like); salts with basic or acidic amino acids (e.g., arginine, aspartic acid, glutamic acid and the like), and the like can be mentioned.

The configuration (absolute configuration) of α carbon atom in compounds [I] and [II] is not particularly limited and the compounds may be an L form, a D form, racemate and the like, with preference given to L forms of compounds [I] and [II].

When an asymmetric carbon atom is present besides α carbon atom, enantiomers and diastereomers due to the asymmetric carbon atom may be present. The present invention encompasses all these isomers and a mixture thereof.

The compound [II] and a salt thereof can be produced by a method known to those of ordinary skill in the art, such as protection of amino group in tyrosine and the like.

As compound [II] or a salt thereof, N-Boc-tyrosine and N—Ac-tyrosine are preferable, wherein Boc is a tert-butoxycarbonyl group and Ac is an acetyl group, and N-Ac-tyrosine is more preferable from an economic aspect.

As the salt of compound [III], the salts recited for the salts of the above-mentioned compounds [I] and [II], and the like can be mentioned.

As compound [III] or a salt thereof, benzyl chloride, benzyl bromide and 2-picolyl chloride hydrochloride are preferable.

The amount of compound [III] to be used is 1–2 mol, preferably 1.1–1.4 mol, per 1 mol of compound [II] or a salt thereof.

As the "alcohol", straight or branched alcohol having 1 to 4 carbon atoms is preferable, such as methanol, ethanol, isopropanol, tert-butanol and the like.

From the economical aspect and versatility, methanol and ethanol are preferable, and methanol is particularly preferable.

The amount of alcohol to be used is, for example, 1 L–10 L, preferably 2 L–8 L, more preferably 3 L–5 L, per 1 kg of compound [II] or a salt thereof.

As the base, alkali metal alkoxide is preferable.

The alkali metal alkoxide is preferably sodium alkoxide prepared from sodium and the above-mentioned alcohol, such as sodium methoxide, sodium ethoxide, sodium isopropoxide, sodium tert-butoxide and the like.

From the economical aspect, versatility and handling property, sodium methoxide and sodium ethoxide are preferable, and sodium methoxide is particularly preferable.

The alcohol moiety of alkali metal alkoxide to be used in the present invention is desirably the same as the alcohol solvent to be used for reaction.

The amount of the base to be used is 2–5 mol, preferably 2–4 mol, more preferably 2–3 mol, per 1 mol of compound [II] or a salt thereof.

When compound [III] is a salt, [(molar amount of compound [III])×(the number of functional group(s) forming salt in compound [III])] mol of a base is additionally necessary.

For example, when compound [III] is a salt of a hetero ring-methylene halide, such as picolyl chloride (e.g., 2-picolyl chloride hydrochloride etc.) and the like, the salt does not need to be converted to a free form for carrying out the reaction of the present invention, and can be used for the reaction as it is by adding a suitable amount of a base.

From the economical aspect and versatility, methanol or ethanol is preferably used as an alcohol, and sodium methoxide or sodium ethoxide is preferably used as a base. It is particularly preferable to use methanol as an alcohol and sodium methoxide as a base.

In the present invention, when $R^4$ is an optionally substituted aryl group and X is a chlorine atom, it is preferable to add a promoter such as n-Bu$_4$NI (tetrabutylammonium iodide), KI, NaI and the like to shorten the reaction time by activation of the reaction.

The amount of the promoter to be used is 0.01–0.5 g, preferably 0.01 g–0.2 g, more preferably 0.01 g–0.1 g, per 1 g of compound [II] or a salt thereof.

The reaction temperature is generally 0° C.–50° C., preferably 20° C.–50° C., more preferably 20° C.–40° C.

The reaction time is generally 1 hr-120 hr, preferably 3 hr–72 hr, more preferably 3 hr–24 hr.

The reaction yield is 75–95%, and can be measured by HPLC (high performance liquid chromatography).

| HPLC conditions | |
|---|---|
| column | ODS-2 (15 cm × 4.6 φmm, GL Sciences Inc.) |
| eluent | 0.03M aqueous KH$_2$PO$_4$ solution:acetonitrile = 90:10→25:75 (120 min) |
| flow rate | 1 mL/min |
| detection wavelength | 210 nm |
| temperature | 25° C. |

The work up of the reaction can be done by a conventional method known to those of ordinary skill in the art, and isolation and purification can be performed by appropriately selecting a conventional method such as is as crystallization, recrystallization, distillation, partitioning, silica gel chromatography, preparative HPLC and the like, as necessary, or in combination, with preference given to crystal precipitation (crystallization, recrystallization).

EXAMPLES

The present invention is explained in detail in the following by referring to Examples, which are not to be construed as limitative.

Example 1

To a solution of N-Boc-tyrosine (281 mg, 1.0 mmol) in methanol (0.5 mL) were added 28% sodium methoxide-methanol solution (0.42 mL, 2.1 mmol), benzyl chloride (115 μL, 1.4 mmol) and tetrabutylammonium iodide (28 mg) and the mixture was stirred at 40° C. for 24 hr. Then, water (2 mL) was added to make the system homogeneous, which system was then analyzed by HPLC (conversion yield 89%). The aqueous solution was washed with toluene (0.5 mL), neutralized with hydrochloric acid to allow precipitation of a solid, and the solid was filtered and dried to give the objective N-Boc-(O-benzyl)tyrosine (312 mg, yield 84%).

$^1$H-NMR (400 MHz, CDCl$_3$) δ: 1.41(s, 3H), 2.86–3.13(m, 2 H), 4.53(m, 1H), 5.01(s, 2H), 6.35–7.41(m, 9H).

$^{13}$C-NMR (100 MHz, CDCl$_3$) δ: 176.51, 157.99, 136.99, 130.40, 128.58, 127.96, 127.48, 115.00, 80.32, 70.03, 36.93, 28.30.

MS(ESI), m/z 370[M$^+$–H]

Example 2

To a solution of N-Boc-tyrosine (281 mg, 1.0 mmol) in methanol (0.5 mL) were added 28% sodium methoxide-methanol solution (0.42 mL, 2.1 mmol) and benzyl bromide (162 μL, 1.4 mmol), and the mixture was stirred at 40° C. for 3 hr. Then, water (2 mL) was added to make the system homogeneous, which system was analyzed by HPLC. As a result, the objective N-Boc-(O-benzyl)tyrosine (353 mg, conversion yield 95%) was confirmed.

Example 3

To a solution of N-Ac-tyrosine (223 mg, 1.0 mmol) in methanol (0.5 mL) were added 28% sodium methoxide-methanol solution (0.42 mL, 2.1 mmol), benzyl chloride (99 μL, 1.2 mmol) and tetrabutylammonium iodide (22 mg), and the mixture was stirred at 40° C. for 24 hr. Then, water (4 mL) was added to make the system homogeneous, which system was then analyzed by HPLC. As a result, the objective N-Ac-(O-benzyl)tyrosine (255 mg, conversion yield 81%) was confirmed. The aqueous solution was washed with toluene (0.5 mL), neutralized with hydrochloric acid to allow precipitation of a solid, and the solid was filtered and dried to give the objective N-Ac-(O-benzyl)tyrosine (244 mg, yield 78%).

$^1$H-NMR (400 MHz, DMSO-d$_6$) δ: 1.78(s, 3H), 2.73–2.98 (m, 2H), 4.35(m, 1H), 5.05(s, 2H), 6.90–7.44(m, 9 H), 8.13(d, 1H).

$^{13}$C-NMR (100 MHz, DMSO-d$_6$) δ: 1730.56, 169.55, 157.37, 137.55, 130.43, 130.15, 128.76, 128.13, 128.03, 114.82, 69.49, 54.07, 36.32, 22.70.

MS(ESI), m/z 314[M$^+$+H]

Example 4

To a solution of N-Boc-tyrosine (281 mg, 1.0 mmol) in methanol (0.5 mL) were added 28% sodium methoxide-methanol solution (0.8 mL, 4.0 mmol) and 2-picolyl chloride hydrochloride (230 mg, 1.4 mmol), and the mixture was stirred at 25° C. for 24 hr. Then, water (3 mL) was added make the system homogeneous, which system was then analyzed by HPLC. As a result, the objective N-Boc-(O-2-picolyl)tyrosine (346 mg, conversion yield 93%) was confirmed.

$^1$H-NMR (400 MHz, CDCl$_3$) δ: 1.39(s, 3 H), 3.18–3.22 (m, 2H), 4.34(m, 1H), 5.16(s, 2H), 6.80–8.59(m, 9H).

$^{13}$C-NMR (100 MHz, CDCl$_3$) δ: 168.45, 157.56, 148.95, 136.89, 130.84, 122.52, 121.34, 114.79, 114.43, 77.35, 70.41, 58.85, 28.42, 23.98.

MS(ESI), m/z 373[M$^+$+H]

Since the production method of the present invention is superior in productivity, versatility and safety, it is preferable for industrial production of O-substituted tyrosine compound.

This application is based on a patent application No. 180265/2004 filed in Japan on Jun. 17, 2004, the contents of which are all hereby incorporated by reference.

The invention claimed is:

1. A method of producing a compound represented by the formula [I] or a salt thereof:

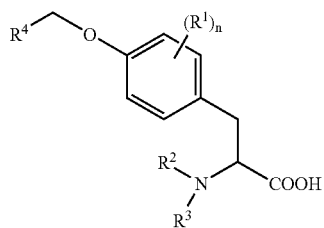

wherein
R$^1$ is each independently a halogen atom, an alkyl group, an alkoxy group or a hydroxy group,
R$^2$ and R$^3$ are each independently a hydrogen atom or an amino-protecting group,
R$^4$ an optionally substituted aryl group or an optionally substituted hetero ring group, and
n is an integer of 0–4,
provided that R$^2$ and R$^3$ are not simultaneously hydrogen atoms,
wherein said method comprises reacting a compound represented by the formula [II] or a salt thereof:

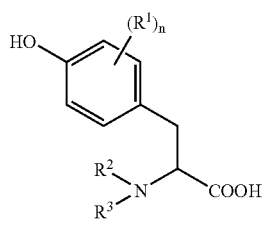

wherein
R$^1$, R$^2$, R$^3$ and n are as defined above,
with a compound represented by the formula [III] or a salt thereof:

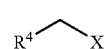

wherein R$^4$ is as defined above, and
X is a halogen atom, a toluenesulfonyloxy group, a methanesulfonyloxy group or a trifluoromethanesulfonyloxy group,
in the presence of an alkali metal alkoxide, in alcohol.

2. The production method of claim 1, wherein the alcohol is selected from the group consisting of methanol, ethanol, isopropanol and tert-butanol.

3. The production method of claim 2, wherein the alcohol is methanol.

4. The production method of claim 1, wherein the alkali metal alkoxide is selected from the group consisting of sodium methoxide, sodium ethoxide, sodium isopropoxide and sodium tert-butoxide.

5. The production method of claim 4, wherein the alkali metal alkoxide is sodium methoxide.

6. The production method of claim 1, wherein the reaction is carried out, in the presence of sodium methoxide, in methanol.

7. The production method of claim 1, wherein n is 0.

8. The production method of claim 1, further comprising deprotecting the R$^2$ or R$^3$ group in formula [I] with an acid.

9. The production method of claim 1, wherein the amino-protecting group for R$^2$ or R$^3$ selected from the group consisting of a tert-butoxycarbonyl group, a benzyloxycarbonyl group, a methoxycarbonyl group, an acetyl group, a benzoyl group and a benzyl group.

10. The production method of claim 1, wherein X is a halogen atom.

11. The production method of claim 10, wherein the halogen atom is a chlorine atom or a bromine atom.

12. The production method of claim 1, wherein said reacting is at a temperature ranging from 20 to 50° C.

13. The production method of claim 1, further comprising washing said compound of formula [I] or salt thereof to remove said compound of formula [III] or salt thereof.

14. The production method of claim 13, wherein said washing comprises addition of water and one or more suitable solvent.

15. The production method of claim 14, wherein said solvent is selected from the group consisting of heptane, toluene, and dichloromethane.

16. The production method of claim 1, further comprising purifying said compound represented by the formula [I], or a salt thereof.

17. The production method of claim 1, wherein, when present, said alkyl is a straight, branched or cyclic alkyl group having 1 to 6 carbon atoms.

18. The production method of claim 1, wherein, when present, said alkoxy is a straight, branched or cyclic alkoxy group having 1 to 6 carbon atoms.

19. The production method of claim 1, wherein the α-carbon of the compound of at least one of [II] or [III], or a salt thereof, is in an L-form.

20. The production method of claim 1, wherein the compound of formula [I] or salt thereof is N-Boc-tyrosine or N-Ac-tyrosine.

21. The production method of claim 1, wherein said compound of formula [III] or salt thereof is added at a concentration ranging from 1 to 2 mol per 1 mol of the compound of formula [II] or salt thereof.

22. The production method of claim 1, wherein said alcohol is present in an amount ranging from 1 to 10 L per 1 kg of compound of formula [II] or salt thereof.

23. The production method of claim 1, wherein said alkali metal alkoxide is present in an amount ranging from 2 to 5 mol per 1 mol of formula [II] or salt thereof.

24. The production method of claim 1, further comprising a reaction promoter in a concentration ranging from 0.01 to 0.5 g per 1 g of compound of formula [II] or salt thereof.

25. The production method of claim 24, wherein said reaction promoter is selected from the group consisting of n-Bu$_4$NI, KI, and NaI.

26. The production method of claim 1, wherein said reacting is for a time ranging from 1 hour to 120 hours.

27. The production method of claim 1, wherein $R^4$ is an optionally substituted hetero ring group.

* * * * *